(12) United States Patent
Kiy et al.

(10) Patent No.: US 6,403,345 B1
(45) Date of Patent: Jun. 11, 2002

(54) OBTAINMENT OF γ-LINOLENIC ACID FROM PROTOZOA OF THE GENUS COLPIDIUM

(75) Inventors: Thomas Kiy, Frankfurt; Kay Brinkmann, München, both of (DE)

(73) Assignee: Aventis Research & Technologies GmbH & Co KG (DE)

( * ) Notice: Subject to any disclaimer, the term of this patent is extended or adjusted under 35 U.S.C. 154(b) by 0 days.

(21) Appl. No.: 09/491,622

(22) Filed: Jan. 26, 2000

(30) Foreign Application Priority Data

Jan. 27, 1999 (DE) .......................... 199 03 095

(51) Int. Cl.$^7$ .............................. C12P 7/64; C12N 1/10
(52) U.S. Cl. .................... 435/134; 435/135; 435/258.1; 435/813; 435/947
(58) Field of Search .............................. 435/258.1, 813, 435/947, 135, 134

(56) References Cited

FOREIGN PATENT DOCUMENTS

| | | |
|---|---|---|
| DE | 198 32 784 | 2/2000 |
| WO | 91/11918 | 8/1991 |

OTHER PUBLICATIONS

Hansson, L, et al, *Appl. Microbiol Biotechnol* 28:240–246 (1988).
Gosselin, Y., et al, *Biotechnology Letters* 11:423–426 (1989).
Lindberg, A–M, et al, *Appl. Microbiol. Biotechnol.* 36:26–28 (1991).
Krištofiková, L., et al, *Folia Microbiol.* 36:451–455 (1991).
Kiy, T., et al, *Appl. Microbiol. Biotechnol.* 37:576–579 (1992).
Deferne, J–L, et al, *Journal of Human Hypertension* 6:113–119 (1992).
Horrobin, D. F, *Prog. Lipid Res.* 31:163–194 (1992).
Mahajan, G., et al, *Appl. Microbiol. Biotechnol* 43:466–469 (1995).
Phillips, J. C., et al, "γ–Linolenic Acid, Metabolism and its Role in Nutrition and Medicine" AOCS, (ed. Huang and Mills), 1996, pp. 106–117 (chapter 1).
Wu, D., et al, "γ–Linolenic Acid, Metalolism and its Role in Nutrition and Medicine," AOCS, (ed. Huang and Mills), 1996, pp. 106–117 (chapter 9).
Das, U. N., "γ–Linolenic Acid, Metabolism and its Role in Nutrition and Medicine," AOCS, (ed. Huang and Mills), 1996, pp. 282–292 (chapter 22).
Kiy, T., *Protist* 149:17–21 (1998).
Craig, B. M., et al, *J. of the American Oil Chemists' Society* 41:209–211 (1964).
Erwin, J., et al, *J. of Biological Chemistry* 238:1618–1624 (1963).
Shaw, R., *Biochimica et Biophysica Acta* 98:230–237 (1965).
Holz Jr., G. G., et al, *Biology of Tetrahymena*, Stroudsburg, PA, 1973, pp. 99–122.
Gibson, R. A., et al, *The American Journal of Clinical Nutrition* 34:252–257 (1981).
Rogerson, A., et al, *Journal of General Microbiology* 124:53–59 (1981).
Rogerson, A., et al, *J. Gen. Appl. Microbiol.* 29:41–50 (1983).
Wolf, R. B., et al, *JAOCS* 60:1858–1860 (1983).
Traitler, H., et al, *JAOCS* 65:755–760 (1988).

*Primary Examiner*—Herbert J. Lilling
(74) *Attorney, Agent, or Firm*—Connolly Bove Lodge & Hutz LLP

(57) ABSTRACT

The present invention relates to a process for the preparation of γ-linolenic acid (GLA) from Colpidium and its use in foodstuffs, cosmetics and pharmaceuticals. Colpidium can be fermentatively cultured up to a high absolute yield of GLA in an optimized medium.

11 Claims, 4 Drawing Sheets

Pylogenetic Tree

- Tetrahymena pigmentosa
- Tetrahymena hegewischi
- Tetrahymena caudata
- Tetrahymena borealis
- Tetrahymena elliotti
- Tetrahymena malaccensis
- Tetrahymena thermophila
- Glaucoma chattoni
- Colpidium campylum

OBTAINMENT OF γ-LINOLENIC ACID FROM PROTOZOA OF THE GENUS COLPIDIUM

BACKGROUND OF THE INVENTION

1. Field of the Invention

The invention relates to a process for the preparation of highly unsaturated fatty acids, preferably of the physiologically important γ-linolenic acid (all-cis 6,9,12-octadecatrienoic acid; 18:3 n-6; below: "GLA") from protozoa of the genus Colpidium and to their use.

2. Description of the Prior Art

The interest of the industry in the obtainment and isolation of fatty acids, in particular of fatty acids which are important (essential) in terms of nutritional physiology, preferably polyunsaturated fatty acids, is great. In particular, the development and selection of novel biological sources which could yield GLA inexpensively are worth particular attention. GLA is mainly obtained, depending on resources, from vegetable oils.

In particular, highly unsaturated fatty acids (so-called "PUFA" for: poly-unsaturated fatty acids) are of economical importance, as they have positive effects (1.) as foodstuff additives (in baby foods and many others; see WO 91/11918), (2.) as pharmaceutical active compounds in a large number of indications and (3.) as constituents of cosmetics.

In human and animal metabolism, delta-6 desaturase is the key enzyme for the synthesis of γ-linolenic acid from linoleic acid (18:2 n-6). All other ω-6 PUFAs and some eicosanoid hormones are derived from GLA. If there is an excessively low activity of the delta-6 desaturase—caused, for example, by age, malnutrition or alcoholism—an undersupply of GLA and its secondary products occurs, as a result of which an number of disorders can be caused.

GLA is therefore used for the human and veterinary treatment of inflammatory and immune diseases (Wu, D., Meydani, S. N., 1996; γ-Linolenic Acid, Metabolism and its role in nutrition and medicine (ed. Huang and Mills), 1996 AOCS, 106–117), in cardiovascular disorders (Deferne, J. L. & Leeds, 1992; J. Hum. Hypertension, 6, 113–119), in particular high blood pressure, diabetes (Horrobin, D. F., 1988; Prog. Lipid Res. 31, 163–194) and certain forms of cancer (Das, U. N, 1996; γ-Linolenic Acid, Metabolism and its role in nutrition and medicine (ed. Huang and Mills), 1996 AOCS, 106–117). The use of GLA is likewise known for the prophylaxis and treatment of chronic, degenerative diseases, in particular rheumatoid arthritis.

Mammals transform GLA into dihomo-GLA (20:3 n-6; DGLA) and concentrate DGLA in mother's milk. In human mother's milk, the content of GLA varies from 0.35 to 1.0% (Gibson, R. A., Kneebone, 1981; Am. J. Clin. Nutr., 34, 252–257). GLA is therefore used in the foodstuffs industry, in particular in infant nutrition.

The provision of native GLA resources takes place especially in higher plants and in a number of microorganisms (Phillips, J. C., Huang, Y.-S., 1996; γ-Linolenic Acid, Metabolism and its role in nutrition and medicine (ed. Huang and Mills), 1996 AOCS, 106–117), such as:

family: Onagraceae: The seeds of the evening primrose (*Oenothera biennis*) contain up to 24% of oil (Whipkey, A., Simon, J. E., Janick, J., 1988; J. Am. Oil Chem. Soc. 65, 979–984); this contains 7–14% of GLA (Wolf, R. B., Kleiman, R., England, R. E., 1983, J. Am. Oil Chem. Soc. 60, 1858–1860). Evening primrose oil is the most frequently used GLA source for clinical and pharmaceutical applications (Horrobin, D. F. 1992; Prog. Lipid Res. 31, 163–194).

family: Boraginaceae: The seed oils of *Borago officinalis* (borage) and *Symphytum officinale* contain a proportion of GLA of 20–27% (Kleiman, R., Earle, F. R., Wolff, I. A., Jones, Q. 1964; J.Am. Oil Chem. Soc. 41, 209–11). Borage oil, however, has higher amounts of longer-chain, monounsaturated fatty acids and contains toxic unsaturated pyrrolidizine alkaloids.

family: Saxifragaceae: The seeds of the blackcurrant (*Ribes nigrum*) contain up to 19% of GLA (Traitler, H., Wille, H. J., Studer, A., 1988; J. Am. Oil Chem. Soc. 65, 755–760).

GLA-containing oils from fermentation of microorganisms are likewise known, such as:

fungi of the genera

Mortierella (*M. ramanniana*, GLA content of the extractable oil about 25%) (Hansson, L., Dostalek, M., 1988; Appl. Microbiol. Biotechnol.: 28, 240–6)

Mucor (*M. rouxii*, and *M. alpina*, GLA content of the extractable oil about 17%) (Lindberg, A. M., Hansson, L., 1991; Appl. Microbiol. Biotechnol., 36, 26–8; Shimitzu, S., Shinmen, Y., Kawashima, H., Akimoto, K., Yamada, H., 1988; Proceedings of ISF-JOCS World Congress 1988, 1000–6);

Phycomycetes (*P. blakesleeanus*, GLA content of the extractable oil about 16%) (Shaw, R., 1965; Biochim. Biophys. Acta, 98, 230–7);

Rhizopus arrhizus (Kristofikova, L., Rosenberg, M., Vinova, A., Sajbidor, J., Certik, M., 1991; Folia Microbiol., 36, 451–5)

"algae" of the genus

Spirulina (*S. platensis*, GLA content of the extractable oil 12–26%) (Mahajan G., Kamat, M., 1995; Appl. Microbiol. Biotechnol., 43, 466–9; Nichols, B. W., Wood, B. J. B., 1968; Lipids, 3, 46–50), and also protazoa of the genus Tetrahymena rostrata: GLA content of the extractable oil about 21% (according to: Gosselin, Y., Lognay, G., Thonart, P., 1989; Biotechnol. Lett., 11 (6), 423–6) *Tetrahymena thermophila*, GLA content of the extractable oil about 33% (according to Kiy, T., 1993; Dissertation).

Compared with the other biological organisms mentioned, the protozoa are not described much as sources for the obtainment of highly unsaturated fatty acids and to a very great extent are undeveloped for industrial obtainment of GLA.

Their advantages compared with the other known biological sources consist (1.) in a multiplicity in each case of characteristic fatty acid spectra with, in some cases, a predominant main component in the oil;

(2.) possible culturability in a bioreactor, fermentation;

(3.) culturing which can be controlled accurately during fermentation, i.e. is independent of environmental influences;

(4.) and a defined working-up process following the fermentation;

(5.) if the generation times are significantly shorter than in plants and fungi, such that higher space-time yields result in production.

Fermentation of bacteria, cyanobacteria, algae, fungi and cell cultures from multicellular tissues of plant or animal origin are described in the prior art, but their concentration, working up and purification, e.g. within a fermentation, are not transferable to protozoa.

Fermentation conditions for protozoa (Kiy, Protist, 149, 1998) have only been developed recently. Thus the fermentation of Tetrahymena species is described, which, however, is not transferable to other related species within the protozoa. A disadvantage is moreover the wide fatty acid spectrum with a number of unsaturated fatty acids which are technically complicated to separate (cf. FIG. 1) and does not specify the obtainment of GLA. In other protozoa, such as *Paramecium caudatum* and *Colpoda steini* (Dembitskii, V. M., Zharikova, N. I. Inst. Zool. Tolyatti, USSR. Khim. Prir. Soedin. (1998) 2, 294–5), it was only possible to detect traces of GLA.

In the case of the desired industrial production, the impurities of the chosen biological source therefore adversely affect the quality of the GLA-containing biomass obtained. This can bring about an adverse effect on the prophylactic and medicinal action mentioned and therefore necessitates a complex enrichment and purification. Moreover, if the GLA to be obtained is to be employed as a foodstuff and medicament, a biological source is needed for this which is not pathogenic, in particular not a human pathogen.

In addition, it is necessary to establish an economical, inexpensive production together with purification which makes possible industrial utilization.

The object of the present invention is therefore a process for the preparation of GLA from protozoa, in the purest possible enriched form.

SUMMARY OF THE INVENTION

The object is surprisingly achieved by the specific selection of the protozoa of the genus Colpidium, the species *Colpidium campylum* being particularly preferred. Colpidium has a high GLA content in the fatty acid spectrum (cf. FIG. 3). The GLA fraction is free of contamination in the form of other fatty acids which are similar in their properties to GLA (such as ALA), as a result of which the purification of the GLA is directly facilitated and GLA is obtainable inexpensively from the biomass in pure form. This is particularly marked if the industrial production of this unsaturated fatty acid is carried out with the aid of a chromatographic process.

DESCRIPTION OF THE PREFERRED EMBODIMENTS

Protozoa within the meaning of this invention are those systematized as follows (according to Cavalier Smith, T. (1995), Cell cycles diplokaryosis and the archezoan origin of sex; arch. Protistenk., 145 (3–4) 189–207):
"Kingdom Protozoa" having the families:
1. Percolozoa
2. Parabasalia
3. Euglenozoa
4. Mycetozoa
5. Entamoeba
6. Opalozoa
7. Dinozoa
8. Apicomplexa
9. Ciliophora
10. Haplosporidia
11. Paramyxia
12. Rhizopoda
13. Reticulosa
14. Heliozoa
15. Radiozoa
16. Amoebozoa
17. Choanozoa Within the protozoa, the genus Colpidium, in particular *Colpidium campylum*, is preferred according to the invention from Ciliophora (also: "ciliates"), as Colpidium is not a human pathogen. The invention therefore relates to the use of the genus Colpidium as a biological source for the obtainment and isolation of GLA.

In particular, Colpidium, advantageously for protozoa, has a large cell diameter of 50 $\mu$m (cf. Tetrahymena: about 25 $\mu$m), which can be utilized specifically for higher space-time yields in preparative biomass production, in particular in culturing and fermentation. Moreover, the optimum of the fermentation preferably lies at 19–28° C., 22–25° C. being particularly preferred (cf. Tetrahymena: about 30° C. (Kiy, Tiedtke, Appl. Microbiol. Biotechnol, 37 (1992)).

Colpidium has a significant phylogenetic detachment from the genus Tetrahymena identified as a GLA producer (FIG. 2).

The first culturing of the protozoa *Colpidium campylum* has been carried out by Rogerson and Berger (Rogerson, A., Berger, J., 1981; J. Gen. Microbiol., 124, 53–9; Rogerson, A., Berger, J., 1983; J. Gen. Appl., Microbiol., 29, 41–50), which yields a maximum cell density of $3 \times 10^3$ cells/ml and a generation time of 8–14 h in bacteria-containing (monoaxenic) medium.

Within the meaning of this invention, the novel GLA production and isolation or GLA preparation from the biomass of Colpidium can be carried out directly or be obtained via an oil obtainable from the biomass—in particular the lipid fraction, which in turn allows GLA to be obtained in pure form (GLA according to the invention below). The GLA is obtained directly or from a lipid (such as glycolipids or phospholipids, inter alia) by means of acidic catalysis or hydrolysis with ester cleavage.

The invention therefore likewise relates to lipids containing the biomass and/or oil as such.

Biomass is understood on the one hand as meaning a precursor of protozoa of the genus Colpidium as such, and treated protozoa of the genus Colpidium fermented and cultured according to the invention (see example). Both biomass and oil, in particular lipid fractions, and the GLA purified therefrom can be used in pure form as a raw material and additive or auxiliary for foodstuffs, pharmaceuticals or cosmetics.

The invention therefore likewise relates to a pharmaceutical comprising the GLA according to the invention from the above biomass and/or oil and/or in pure form and, if appropriate, pharmaceutically acceptable additives and/or auxiliaries.

The invention furthermore relates to a process for the production of a pharmaceutical for the human and/or veterinary treatment of cardiovascular disorders, diabetes, cancer and arthritis, which comprises formulating the GLA according to the invention with pharmaceutically acceptable additives and/or auxiliaries. The invention furthermore relates to a foodstuff additive in animal and human nutrition comprising the GLA according to the invention, preferably in very pure form for infant nutrition.

The invention likewise relates to a cosmetic base and/or additive comprising the GLA according to the invention.

The supercritical fluid reaction (SFR) process is particularly suitable as a preferred process for the obtainment of oil and/or GLA in very pure form. In a particular embodiment, the preparation of GLA is carried out by means of combined SFR/SFE (supercritical fluid extraction) technology as described in German Patent Application 198 32 784.6, to which reference is expressly made here. However, in principle other chromatographic processes which are known to the person skilled in the art are also not excluded.

The invention further relates to the fermentation and culturing of Colpidium for the production and isolation of the GLA according to the invention in a complex (i.e. not deficient) and axenic (i.e. without nutrient organisms) medium, which contains up to 1–5%, particularly preferably 0.5–2.5% and very particularly preferably 2% of skimmed milk powder, in addition to a vitamin (e.g. yeast extract) and carbohydrate source (see example) and further auxiliaries and additives.

The following examples serve to explain the invention in greater detail, without the latter being restricted to products and embodiments described in the examples.

EXAMPLES a.) Culturing
Skimmed milk medium:

| | |
|---|---|
| 2 % (w/v) | of skimmed milk powder (Oxoid, Unipath, Wesel) |
| 0.5 % (w/v) | of yeast extract (Difco, Detroit, USA) |
| 1 % (w/v) | of glucose (autoclaved separately) |
| 0.1 % (v/v) | of trace iron solution |
| in | $H_2O$ (double-distilled) |

Trace iron solution:

| | |
|---|---|
| 34 mM | trisodium citrate |
| 90 mM | $FeCl_3$ |
| in | $H_2O$ (double-distilled) |

Long-term culturing:

In the dark at 25° C. in a test-tube with 12 ml of double-distilled $H_2O$ and a chick-pea, autoclaved; transfer of 200 µl of this culture into a new tube every three months.

Preculture:

Shaking (60 rpm, Infors shaking bank, Bottmingen) of 10 ml of MM in a 100 ml Erlenmeyer flask at 25° C., in the dark; after 3.5 d (late log. growth phase), it is possible to inoculate afresh with 200 µl of this culture.

Shaking culture:

Shaking (100 rpm, Infors HT, Infors, Bottmingen) of 100 ml of MM in a 500 ml Erlenmeyer flask at 25° C., in the dark; after 3.5 d the late-logarithmic growth phase is reached.

b.) Fermentation

The fermentation of Colpidium using the Biostat Q bioreactor system (B. Braun Biotech International, Melsungen) is carried out under these conditions:

pH constant at 7.0
temperature constant at 22–31° C.
$p(O_2) > 20\%$ air saturation
speed of rotation of the magnetic stirrer:
   100 rpm with a volume of 0.33 l, or
   at most 280 rpm with a volume of 0.66 l (disc agitator or propeller stirrer) depending on the $p(O_2)$ After in situ sterilization of the fermenter and addition of the glucose solution, inoculation is carried out with an initial cell density of $1 \times 10^5$ cells/ml from shaker cultures of the later-logarithmic growth phase.

In the case of formation of foam during the fermentation, up to at most 0.03% of silicone oil is added.

c.) Analycal Methods

Aliquots are regularly taken from the proceeding fermentation and extracted with toluene/ethanol and the extract is dissolved in dichloromethane/methanol. The samples are transesterified with trimethylsulfonium hydroxide (TMSH) (50–100 µl of TMSH/2 mg of oil). Preferably, a direct transesterification of the lyophilized dry biomatter (DBM) is carried out.

The fatty acid methyl esters obtained are analyzed by gas chromatography using an HP 6890 series gas chromatograph, HP G1512A Automatic Liquid Sampler with a flame ionization detector (HP FID) and a polar capillary column containing chemically bonded PEG-2 nitrophthalic acid ester (Permabond FFAP, length 25 m, diameter 250 µm, film thickness 0.1 µm, Macherey-Nagel GmbH, Düren, Germany). The identification and quantification of the fatty acids is carried out by comparison of the retention times obtained with those of known fatty acid methyl esters, specifically computer-assisted by the HP Chem Station (Hewlett-Packard Company, Wilmington, USA).

In comparison to the industrially carried out obtainment of GLA from vegetable oils, the GLA production using ciliates fundamentally has a significantly higher space-time yield owing to the short generation times and higher absolute GLA contents.

A comparison of the yield of 300 mg of GLA/l of culture obtained from *Colpidium campylum* with established processes for GLA production from microorganisms confirms this high potential as a GLA producer. From shaker cultures of the microalga *Spirulina platensis,* it has previously been possible to obtain only 38 mg of GLA/l of culture (Mahajan G., Kamat, M., 1995; Appl. Microbiol. Biotechnol., 43, 466–9), cultures of the fungus *Mucor rouxii* (Lindberg, A. M., Hansson, L., 1991; Appl. Microbiol. Biotechnol., 36, 26–8) and *Rhizopus arrhizus* (Kristofikova, L., Rosenberg, M., Vinova, A., Sajbidor, J., Certik, M., 1991; Folia Microbiol., 36, 451–5) achieved yields of up to 330 and 400 mg of GLA/l of culture respectively. Fermentation of the ciliate *Tetrahymena rostrata* (Gosselin, Y., Lognay, G., Thonart, P., 1989; Biotechnol. Lett., 11 (6), 423–6) afforded a maximum yield of 500 mg of GLA/l of culture, mass culturing of *Tetrahymena thermophila* (Kiy, T., 1993; Dissertation, Universität Münster) in skimmed milk medium achieved 1.1 g of GLA/l of culture. However, the lipid composition from the latter organisms is more complex than from Colpidium, as a result of which the preparative obtainment of GLA from Tetrahymena is complicated.

GLA elutes after 18.2 min. It has a proportion of 16.3% (w/w) in the total fatty acid content.

Figure 1:
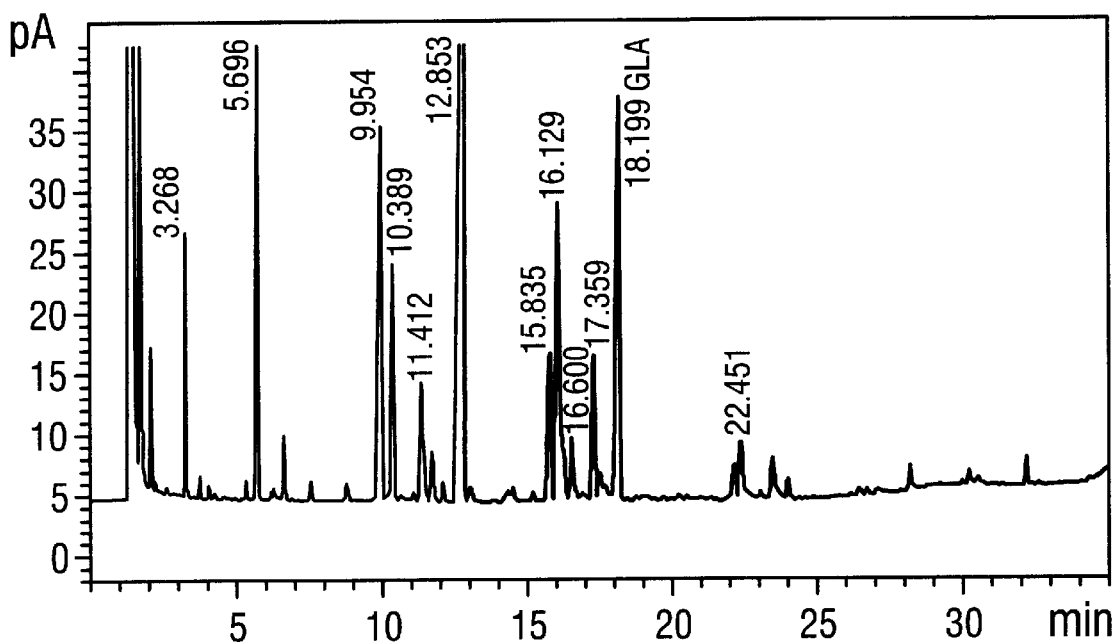
FIG. 1 shows the fatty acid spectrum of *Tetrahymena thermophila*. Gas chromatogram of the fatty acid spectrum of *Tetrahymena thermophila* obtained according to the method described in the section "Analytical methods".
Figure 2:
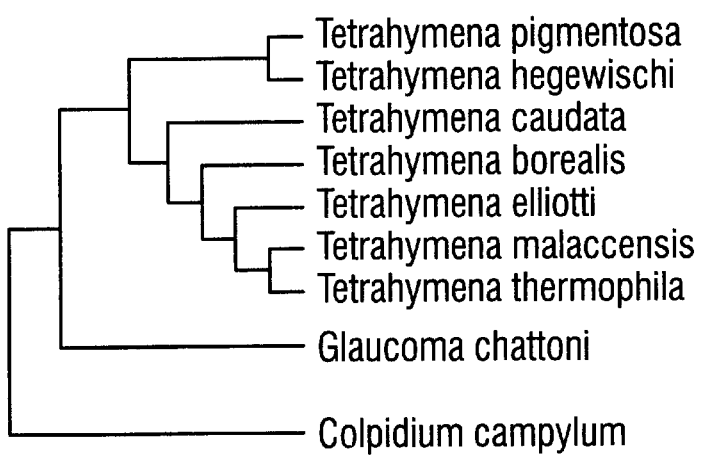

FIG. 2 shows the phylogenetic pedigree of various ciliate species according to: Coyne, R. S., Yao, M.-C., 1996; Genetics, 144:14779–87

Figure 3:
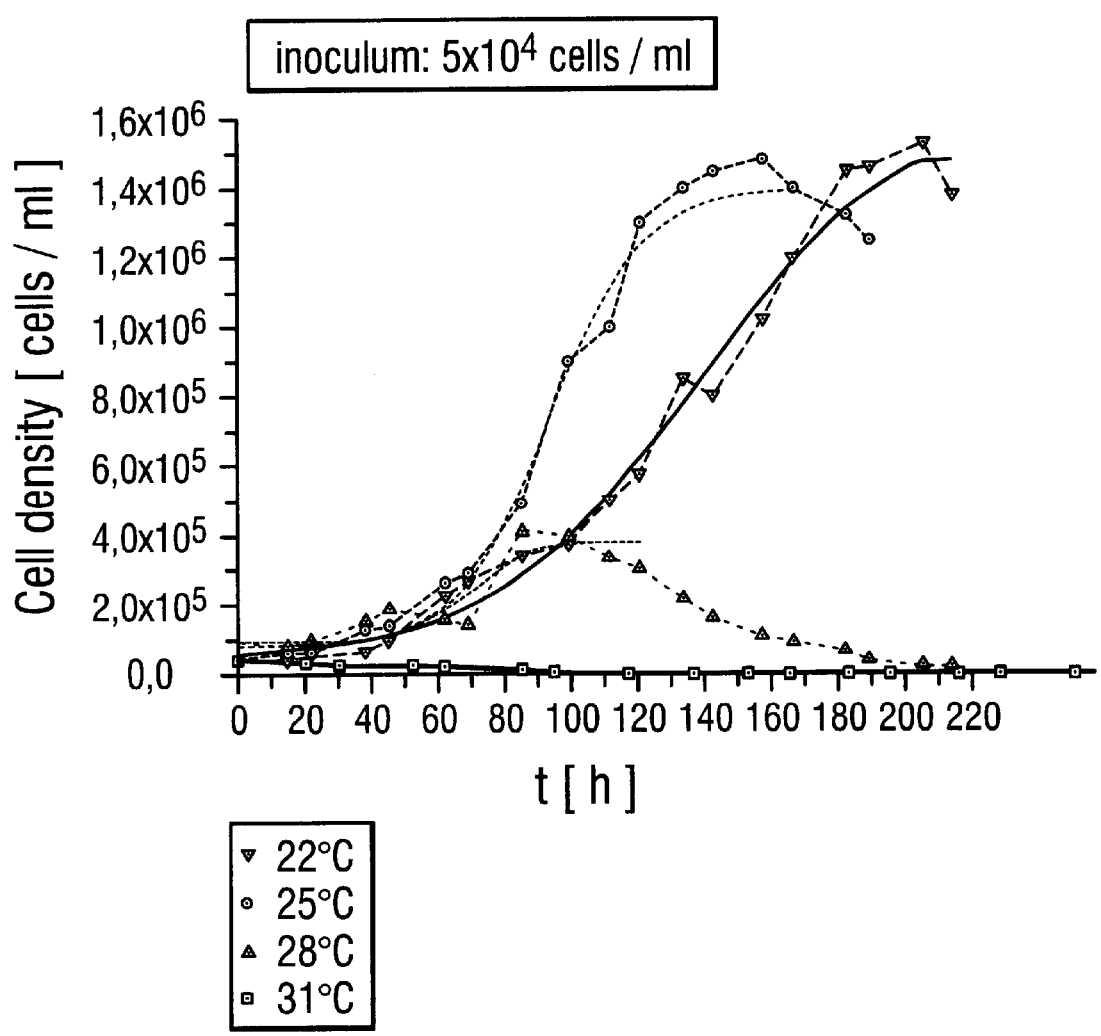

FIG. 3 shows the fermentation of *C. campylum* at 22° C.–31° C.; inoculum in each case $5 \times 10^4$ cells/mol. The shortest generation time is obtained at 25° C. (20.8 h) with a maximal cell density of $1.4 \times 10^6$ ml$^{-1}$. At 22° C., however, a cell density of $1.5 \times 10^6$ ml$^{-1}$ is obtained with a generation time of 45.4 h.

Figure 4:
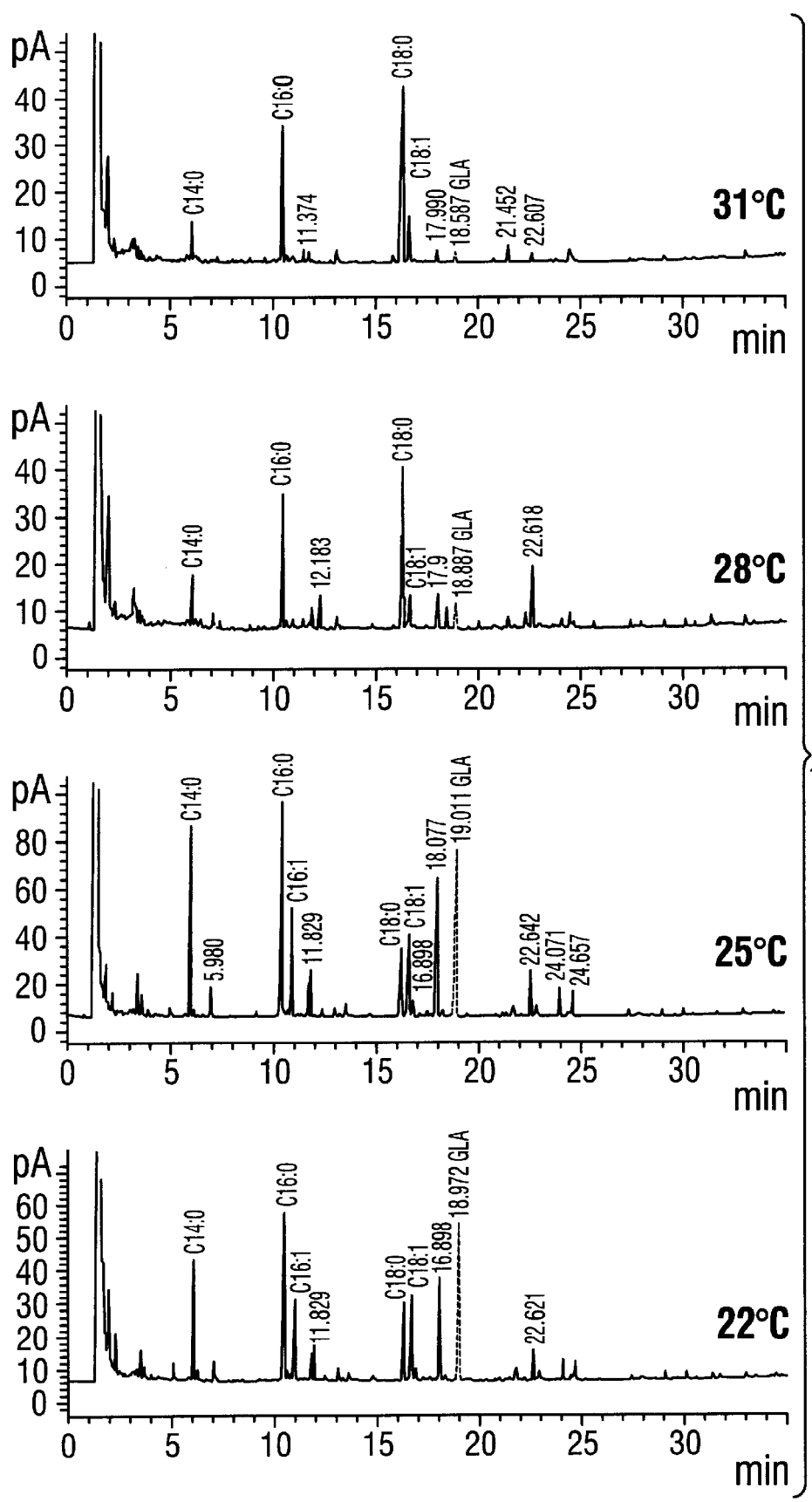

FIG. 4 shows the gas chromatogram after an 85 h fermentation at 25° C. (cf. corresponding to FIG. 3). GLA content is 19% on total lipid; this is 5 mg of GLA per g of dry biomass (DBM), or 50 mg of GLA per l of culture medium.

Figure 5A:
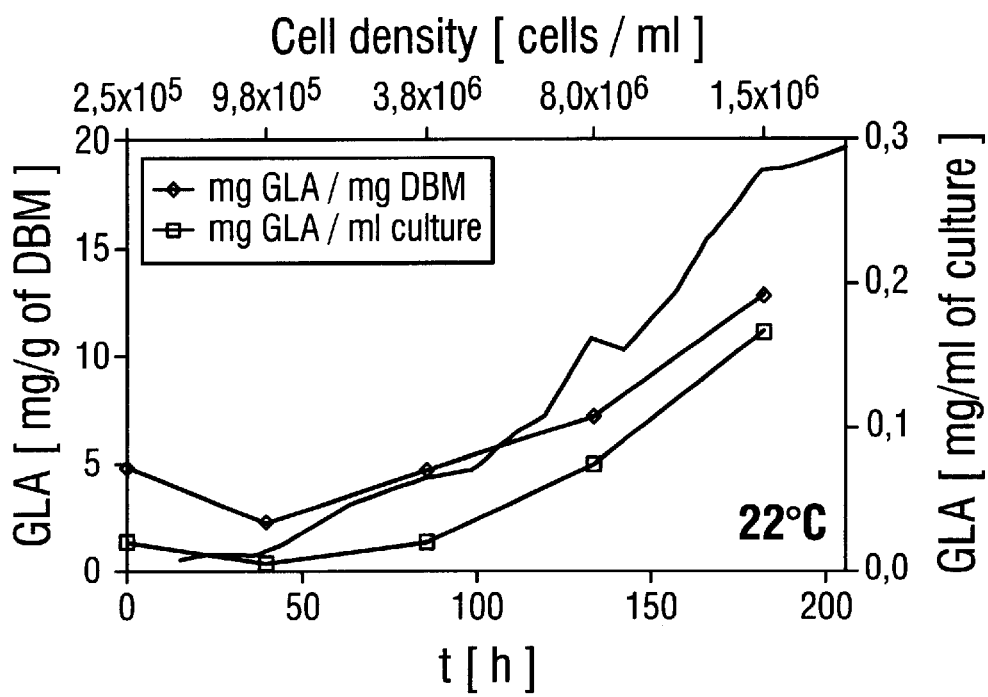
Figure 5B:
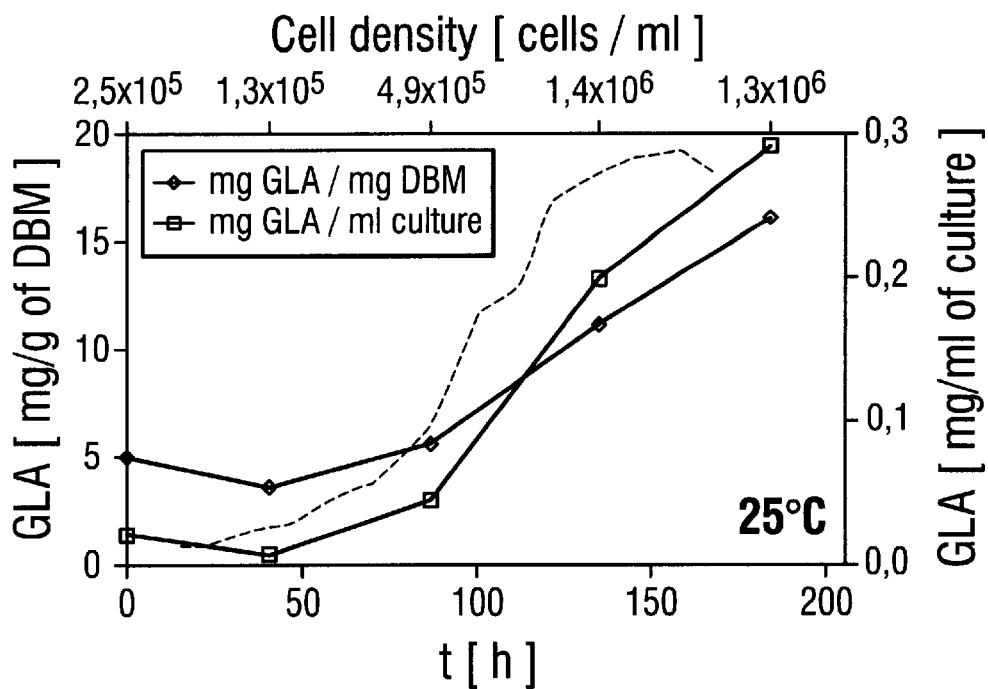

FIGS. 5A and B show how the GLA production develops in the course of fermenation at 22 and 25° C.: (B) Maximum absolute GLA content is established in the early stationary growth phase at a cell density of $1.4 \times 10^6$ ml$^{-1}$.

On fermenation under optimal growth conditions (25° C.), the relative fatty acid composition of the *C. campylum* cultures shifts from a high proportion of saturated fatty acids to a high GLA content. During the lag phase, 15% of GLA is present. As the maximum relative GLA value, 19% of GLA are obtained in the logarithmic phase after about 160 h; on fermentation at 22° C. even 25%; in this case, however, on account of the slower growth and about 50 h later than at 25° C. On further culture, the relative GLA content decreases again.

The highest quantitative GLA yields are obtained at the culturing temperature of 25° C., namely after a 185 h fermentation, in the stationary phase: 13 mg GLA/g of DBM and 290 mg of GLA/l of culture. This is opposed to at most 7 mg of GLA/g of DBM and 170 mg of GLA/l of culture at a temperature of 22° C., namely after a fermentation time of 220 h.

The highest relative GLA contents of *C. campylum* are achieved in the logarithmic growth phase, the highest absolute GLA contents, however, after the transition from the growth phase to the stationary phase. This is explained—in addition to achieving the maximum cell density—by an increase in the total fat content in the stationary phase (Erwin, J., Bloch, K., 1963; J. Biol. Chem., 238 (5), 1618–24; Holz, G. G., Conner, R., 1973; Biology of Tetrahymena; Stroudsburg, Pa.).

What is claimed is:

1. A process for preparing γ-linolenic acid, comprising:

(i) culturing and fermenting a protozoa of the genus Colpidium and (ii) obtaining the γ-linolenic acid from the culture in the form of a biomass.

2. A process according to claim 1, wherein the γ-linolenic acid is obtained in the form of a lipid-fraction isolated from the biomass.

3. The process as claimed in claim 1, wherein the culturing and fermenting are carried out at a temperature of from 19 to 28° C.

4. A process according to claim 1, wherein the γ-linolenic acid is purified from the lipid fraction by acid catalysis or hydrolysis with ester cleavage.

5. The process as claimed in claim 1, further comprising chromatographically obtaining and isolating the γ-linolenic acid.

6. The process as claimed in claim 3, wherein the temperature is from 22 to 25° C.

7. The process as claimed in claim 1, wherein the culturing and fermenting steps are carried out in a complex and axenic medium comprising:

a) up to 5% of a skimmed milk powder, b) a vitamin, c) a carbohydrate source, d) optionally, an auxiliary; and e) optionally, an additive.

8. The process as claimed in claim 7, wherein from 0.5 to 2.5% of the skimmed milk powder is present.

9. The process as claimed in claim 8, wherein 2% of the skimmed milk powder is present.

10. The process as claimed in claim 7, wherein the vitamin is a yeast extract.

11. The process as claimed in claim 7, wherein the carbohydrate source is glucose.

* * * * *